United States Patent
Venturelli

(10) Patent No.: US 6,635,029 B1
(45) Date of Patent: Oct. 21, 2003

(54) DILATION CATHETER STRUCTURE

(75) Inventor: Andrea Venturelli, Concesio (IT)

(73) Assignee: Invatec S.r.l. (IT)

( * ) Notice: Subject to any disclaimer, the term of this patent is extended or adjusted under 35 U.S.C. 154(b) by 0 days.

(21) Appl. No.: 09/311,498

(22) Filed: May 13, 1999

(51) Int. Cl.⁷ .................. A61M 3/00; A61M 29/00; A61M 31/00; A61M 37/00
(52) U.S. Cl. ............ 604/43; 604/96.01; 604/103.04
(58) Field of Search .............. 604/43, 97.01, 604/103.04, 96.01, 264

(56) References Cited

U.S. PATENT DOCUMENTS

| | | | | |
|---|---|---|---|---|
| 4,552,554 A | * | 11/1985 | Gould et al. ............ | 604/104 |
| 5,102,403 A | | 4/1992 | Alt | |
| 5,156,594 A | * | 10/1992 | Keith ................. | 604/103.09 |
| 5,176,689 A | * | 1/1993 | Burns et al. ............ | 606/192 |
| 5,306,247 A | * | 4/1994 | Pfenninger ........... | 604/102.02 |
| 5,364,376 A | * | 11/1994 | Horzewski et al. ....... | 604/528 |
| 5,389,087 A | * | 2/1995 | Miraki ................. | 604/160 |
| 5,545,134 A | * | 8/1996 | Hilaire et al. .......... | 604/103.04 |
| 5,571,087 A | * | 11/1996 | Ressemann et al. ....... | 604/264 |
| 5,667,493 A | * | 9/1997 | Janacek ............... | 604/96.01 |
| 5,755,685 A | * | 5/1998 | Andersen .............. | 604/103.04 |
| 5,769,868 A | * | 6/1998 | Yock .................. | 606/194 |
| 5,823,995 A | * | 10/1998 | Fitzmaurice et al. ..... | 604/103.06 |
| 5,846,246 A | * | 12/1998 | Dirks et al. ........... | 604/103.04 |
| 6,004,291 A | * | 12/1999 | Ressemann et al. ....... | 604/523 |
| 6,030,405 A | * | 2/2000 | Zarbatany et al. ....... | 174/95 |
| 6,059,713 A | * | 5/2000 | Urick et al. ........... | 600/3 |
| 6,190,358 B1 | * | 2/2001 | Fitzmaurice et al. ..... | 604/102.02 |

FOREIGN PATENT DOCUMENTS

EP    712 639 A2    5/1996

* cited by examiner

*Primary Examiner*—Henry Bennett
*Assistant Examiner*—Kathryn Ferko
(74) *Attorney, Agent, or Firm*—McGlew and Tuttle, P.C.

(57) ABSTRACT

A dilation catheter structure of the rapid exchange is provided with an inflatable balloon and with a lumen for a guide thread. The catheter comprises a distal tube (12) and a guide tube (13). The guide tube (13) extends into the distal tube (12), and the proximal ends (13', 12') of the guide tube (13) and the distal tube (12) are joined to one another and at the distal end (11') of the main tube (11). The proximal end (13') of the guide tube (13) has an opening on one side of the main tube (11) and the proximal end (12') of the distal tube (12) reaches the distal end of the main tube and the proximal end of the guide tube tightly and simultaneously.

15 Claims, 1 Drawing Sheet

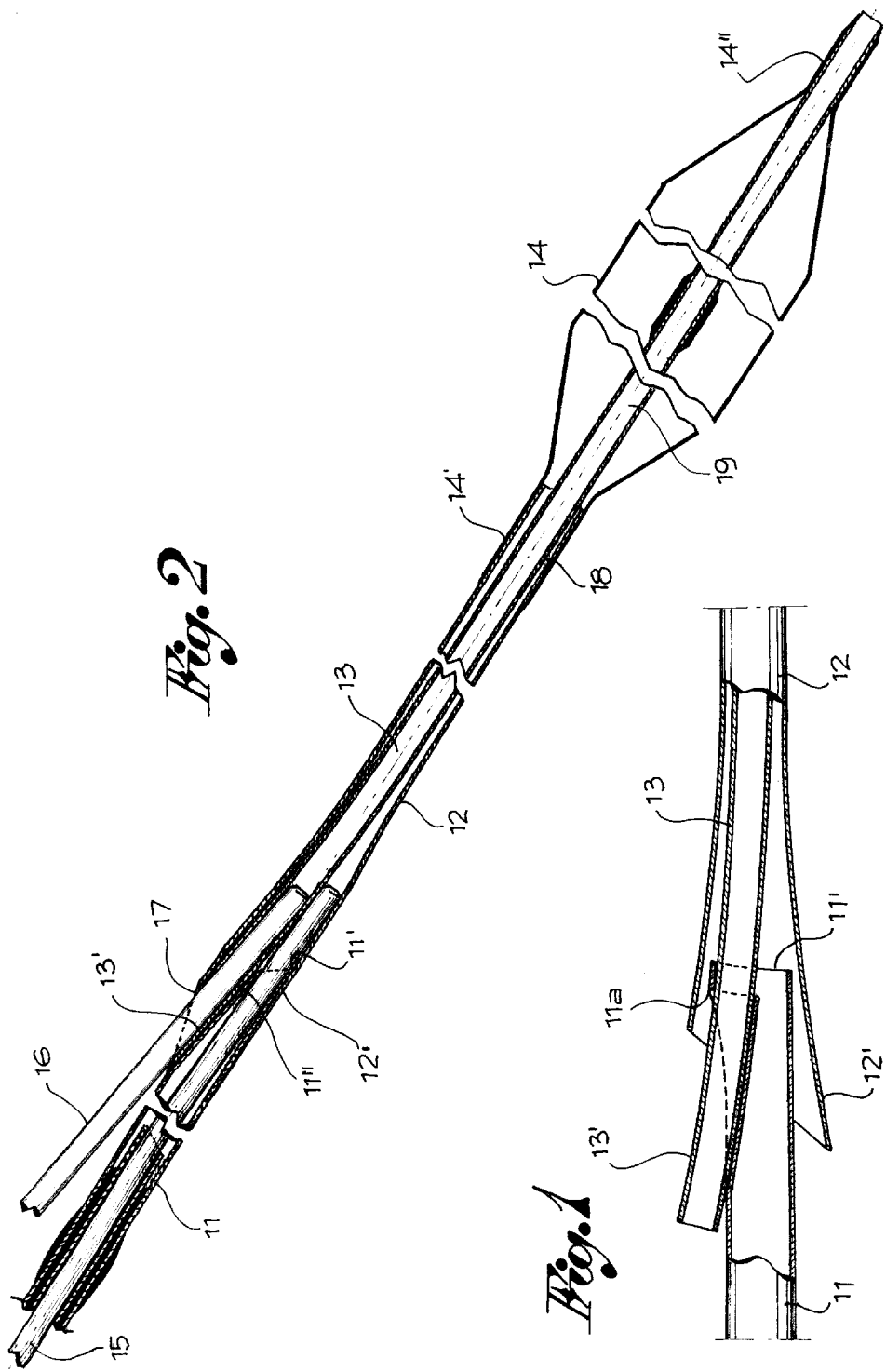

DILATION CATHETER STRUCTURE

FIELD OF THE INVENTION

The present invention pertains to dilation catheters of the so-called rapid exchange type with an inflatable balloon and with a lumen for a guide thread.

BACKGROUND OF THE INVENTION

These catheters can be used in various operating and surgical procedures and/or for inserting molds, called stents, inside the ducts or lumens of a live body.

A dilation catheter generally comprises a thin and extended tubular element and usually has an inflatable balloon near its distal end, a first lumen for a guide thread and at least a second lumen for the passage of a fluid for inflating the balloon.

In the prior-art designs, the first and the second lumina of the catheter may be coaxial or not, may be made into a single extruded element, separated by a baffle, or formed by two small tubes of different diameter arranged one inside the other.

However, the current trend is to create a point for passing the guide thread in the catheter in a zone close to the distal end even though before, above, the inflatable balloon in order to reduce or preferably balance the sliding force of the catheter along the guide thread during the insertion in the body.

Various embodiments of dilation catheters have already been proposed in order to meet such a requirement.

In one embodiment, the catheter has a single extruded body, which has two integral lumina (e.g., EP-A-0 712 639) with one lumen for inflating the balloon and another lumen for the guide thread, this second lumen simply having a radial opening for the passage of the guide thread above the balloon.

According to another embodiment, a first and a second lumen of the catheter (e.g., U.S. Pat. No. 5,102,403) are obtained, in a distal section from the front of the balloon of the catheter, by means of a longitudinal deformation of a starting tube which has a single lumen. The deformation is performed along a generating line of the tube and aimed at creating a lumen for the guide thread, which lumen has an opening on one side of the starting tube, which goes deep down to more or less on the axis of the tube, and which opens at the distal end of same, while the lumen proper of the starting tube opens into the balloon.

SUMMARY AND OBJECTS OF THE INVENTION

Starting from these premises the primary object of the present invention is to provide a novel dilation catheter structure produced by means of an original configuration and combination of single tubular elements, therefore not in a single piece obtained from extrusion or deformed as taught by the prior art.

According to the invention, a dilation catheter structure of the rapid exchange type is provided with an inflatable balloon and with a lumen for a guide thread (i.e., the connection strand, filament etc). The structure has a main tube, which has a distal end, a distal tube and a guide tube, in which the guide tube extends in the distal tube. The proximal ends of the guide tube and the distal tube are joined to one another and at the distal end of the main tube. The proximal end of the guide tube has an opening on one side of the main tube. The proximal end of the distal tube encloses the distal end of the main tube and the proximal end of the guide tube tightly and simultaneously.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 1 is a sectional view, before assembly, of parts of the tubes intended to form the catheter; and FIG. 2 shows a distal part of the assembled catheter and complete with balloon.

DESCRIPTION OF THE PREFERRED EMBODIMENT

Referring to the drawings in particular, the catheter provided by the invention comprises a main tube 11, a distal tube 12, a guide tube 13 and a balloon 14.

The main tube 11 may be a single piece or comprise many tubular parts which are combined consecutively, perhaps different in terms of material and thickness or rigidity, so that the tube has a different flexibility or softness in various parts along its length.

The distal tube 12 is arranged as a continuation of the main tube 11, at the distal end 11' of same and the guide tube 13 is arranged in the distal tube 12. These two additional tubes 12, 13 may be of identical or different materials and thicknesses or rigidities, though different from those of the main tube.

As is shown in the drawing, the proximal end 12' of the distal tube 12 is flared so as to fit on the distal end 11' of the main tube and at the same time to enclose the proximal end 13' of the guide tube 13. Moreover, this same end 13' of the guide tube 13 is put on the outside of the distal end 11' of the main tube, on a part 11" which is deflected and inclined towards the axis of the tube itself, or more preferably and for a greater robustness of the resulting unit, the guide tube 13 is made to pass in an opening 11=aprovided in the main tube as shown in FIG. 1.

The tubes 11, 12, 13 thus arranged and combined are then fixed to one another by means of a heat-sealing operation. To keep the tubes in shape in their zones to be sealed, and thus preventing their collapse and the blocking of their lumina, two expanders 15 and 16 are inserted into the main tube 11 and in the guide tube 13, respectively, which expanders are then extracted once the sealing has been performed.

In particular, the sealing is done in order to seal to one another the contact zones of the guide tube with the main tube and the outer distal tube all around the main tube and the guide tube. After this action, the expanders are extracted, and the initial ends of the guide tube and the distal tube are beveled in 17 as shown in the drawing.

It should be noted that the guide tube 13 extends beyond the front end of the distal tube 12. The balloon 14 is arranged around the guide tube and has two terminal necks 14', 14", one of which is sealed around the front end of the distal tube, the other is sealed around the distal end of the guide tube.

In the catheter thus constructed, the main tube 11 and the distal tube 12 together form a first axial lumen 18, which opens into the balloon 14; the guide tube 13 forms a second lumen 19 which has an opening on one side of the catheter, at the level of the bevel 17, and an axial opening at the front end of the guide tube itself.

The first lumen 18 is used to send an inflation fluid into the balloon, while the second lumen is used for passing a guide thread, which is usually used to facilitate the introduction of the catheter into the duct in question.

While a specific embodiment of the invention has been shown and described in detail to illustrate the application of the principles of the invention, it will be understood that the invention may be embodied otherwise without departing from such principles.

What is claimed is:

1. A dilation catheter structure of the rapid exchange type provided with an inflatable balloon and with a lumen for a guide thread, the structure comprising:
   a main tube having a distal end;
   a distal tube having a proximal end; and
   a guide tube having a proximal end, said guide tube extending in said distal tube, and said proximal end of said guide tube and said proximal end of said distal tube being functionally connected and disposed adjacent to one another at a location adjacent to said distal end of said main tube, said proximal end of said guide tube having an opening on one side of said main tube, said proximal end of said distal tube enclosing said distal end of said main tube and said proximal end of said guide tube tightly and simultaneously, wherein:
   said distal end of said main tube has a lateral opening;
   said proximal end of said guide tube extends into said lateral opening of said main tube and into said distal tube; and
   said proximal end of said distal tube is flared in order to peripherally surround said guide tube extending into said distal end of said main tube.

2. A dilation catheter structure of the rapid exchange type provided with an inflatable balloon and with a lumen for a guide thread, the structure comprising:
   a main tube having a distal end;
   a distal tube having a proximal end; and
   a guide tube having a proximal end, said guide tube extending in said distal tube, and said proximal end of said guide tube and said proximal end of said distal tube being functionally connected and disposed adjacent to one another at a location adjacent to said distal end of said main tube, said proximal end of said guide tube having an opening on one side of said main tube, said proximal end of said distal tube enclosing said distal end of said main tube and said proximal end of said guide tube tightly and simultaneously, wherein:
   said distal end of said matin tube has apart, which is deflected and inclined towards an inside of said main tube;
   said proximal end of said guide tube rests on the outside of said inclined part of said main tube; and
   said proximal end of said distal tube is flared in order to peripherally surround both said distal end of said main tube and said guide tube extending into said main tube.

3. The catheter structure in accordance with claim 1, wherein said proximal ends of said guide and distal tubes are beveled at said lateral opening of said guide tube.

4. The catheter structure in accordance with claim 1, wherein said guide tube extends beyond a front end of said distal tube, and said balloon is arranged between said two tubes, with a terminal neck fixed to said guide tube and another terminal neck fixed to said distal tube.

5. The catheter structure in accordance with claim 4, wherein said main tribe and said distal tube together form a first lumen for sending an inflation fluid into said balloon, and said guide tube forms a second lumen for the passage of a guide thread.

6. The catheter structure in accordance with claim 1, wherein said main tube comprises tubular sections having at least one of different material compositions, different thicknesses and different rigidities, and said guide tube and said distal tube are formed of materials that different from one another and different from said main tube.

7. The catheter structure in accordance with claim 1, wherein said main tube comprises tubular sections having at least one of different material compositions, different thicknesses and different rigidities, and said guide tube and said distal tube are formed of the same material.

8. The catheter structure in accordance with claim 2, wherein said proximal ends of said guide tube and said distal tube are joined to one another and to said distal end of said main tube by means of heat sealing.

9. The catheter structure in accordance with claim 1, wherein said proximal ends of said guide tube and said distal tube are joined to one another and to said distal end of said main tube by means of heat sealing.

10. A dilation catheter structure with an inflatable balloon, the structure comprising:
    a main tube having a proximal end and a distal end, said main tube distal end having a lateral opening;
    a distal tube having a proximal end and a distal end; and
    a guide tube having a proximal end and a distal end, said guide tube having a portion extending in said distal tube, a portion of said guide tube adjacent to said guide tube proximal end and a portion of said distal tube adjacent to said distal tube proximal end being positioned together at a location adjacent to said main tube distal end, said guide tube proximal end having an opening on one side of said main tube, a portion of said distal tube adjacent to said distal tube proximal end enclosing both a portion of said main tube distal end and a portion of said guide tube adjacent to said guide tube proximal end and said guide tube proximal end extending into said lateral opening of said main tube and into said distal tube.

11. The catheter structure in accordance with claim 10, wherein:
    said distal tube proximal end is flared in order to peripherally reach both said distal end of said main tube and said proximal end of said guide tube.

12. The catheter structure in accordance with claim 10, wherein said guide tube portion adjacent to said guide tube proximal end and said distal tube portion adjacent to said distal tube proximal end are joined to one another and to said main tube portion adjacent to said main tube distal end by a heat seal.

13. The catheter structure in accordance with claim 10, wherein said guide tube proximal end and said distal tube proximal end are beveled at said lateral opening of said guide tube.

14. The catheter structure in accordance with claim 10, wherein said guide tube extends beyond a front end of said distal tube, and said balloon is arranged between said two tubes, with a terminal neck fixed to said guide tube and another terminal neck fixed to said distal tube.

15. The catheter structure in accordance with claim 14, wherein said main tube and said distal tube together form a first lumen for sending an inflation fluid into said balloon, and said guide tube forms a second lumen for the passage of a guide thread.

\* \* \* \* \*

UNITED STATES PATENT AND TRADEMARK OFFICE
CERTIFICATE OF CORRECTION

PATENT NO. : 6,635,029 B1  Page 1 of 1
DATED : October 21, 2003
INVENTOR(S) : Andrea Venturelli It is certified that error appears in the above-identified patent and that said Letters Patent is hereby corrected as shown below:

<u>Title page,</u>
Insert item:
-- [30]  Foreign Application Priority Data
BS98A000043            May 29, 1998 --

Signed and Sealed this

Twenty-third Day of March, 2004

JON W. DUDAS
*Acting Director of the United States Patent and Trademark Office*